United States Patent [19]
Higgins

[11] Patent Number: 5,735,300
[45] Date of Patent: Apr. 7, 1998

[54] TOOTHPICK

[76] Inventor: Patrick O. Higgins, 214 5th St., Catawissa, Pa. 17820

[21] Appl. No.: 752,287

[22] Filed: Nov. 19, 1996

[51] Int. Cl.[6] ................................................. A61C 15/02
[52] U.S. Cl. .................................... 132/329; 132/321
[58] Field of Search ............................ 132/321, 328, 132/329

[56] References Cited

U.S. PATENT DOCUMENTS

| | | | |
|---|---|---|---|
| D. 270,100 | 8/1983 | Hjalmansson | D28/64 |
| D. 298,175 | 10/1988 | Kwok | D28/64 |
| D. 340,315 | 10/1993 | Morin | D28/64 |
| D. 345,825 | 4/1994 | Arnold | D28/64 |
| 817,978 | 4/1906 | Lickman | 132/329 |
| 1,451,380 | 4/1923 | Thum | 132/329 |
| 1,462,062 | 7/1923 | Browning | 132/329 |
| 2,760,628 | 8/1956 | Briggs | 132/329 |
| 2,762,501 | 9/1956 | Cameron | 132/329 |
| 2,925,087 | 2/1960 | Kucher | 132/328 |
| 3,438,486 | 4/1969 | Pinkas | 132/321 |
| 4,546,782 | 10/1985 | Kucher | 132/329 |
| 4,805,646 | 2/1989 | Shimynkov | 132/329 |
| 5,074,100 | 12/1991 | Lepie | 132/321 |
| 5,560,379 | 10/1996 | Pieczenik | 132/329 |

FOREIGN PATENT DOCUMENTS

| | | | |
|---|---|---|---|
| 2327626 | 12/1973 | Germany | 132/329 |

Primary Examiner—Paul J. Hirsch
Attorney, Agent, or Firm—David L. Volk

[57] ABSTRACT

A main body includes a first arm and a second arm, each extending outwardly from opposite corners of the main body. The first arm and the second arm each include a point and a barb at the end thereof. The main body further includes structure forming a first notch opposite the first arm, and a second notch opposite the second arm.

8 Claims, 4 Drawing Sheets

TOOTHPICK

BACKGROUND OF THE INVENTION

1. Field of the Invention

The present invention relates to personal dental hygiene devices, specifically to an apparatus for dislodging food particles from teeth.

2. Description of the Related Art

Various types of articles for dislodging food particles from between and on the teeth exist in the prior art. Examples include conventional straight wooden toothpicks and conventional dental floss. The pointed ends of toothpicks can be dangerous and can create discomfort when they are inserted at the gum line. Conventional dental floss is cumbersome to use, particularly without a mirror. Both dental floss and toothpicks are somewhat inadequate and cumbersome for cleaning behind the teeth, particularly the front teeth.

SUMMARY OF THE INVENTION

The toothpick of the present invention includes a main body. A first arm and a second arm each extend outwardly from opposite corners of the main body. The first arm and the second arm each include a point and a barb at the end thereof. The main body further includes structure forming a first notch opposite the first arm, and a second notch opposite the second arm. The toothpick may be easily grasped and manipulated to dislodge food particles from teeth using the point and the barb.

Accordingly, several objects and advantages of the present invention are:

a. to provide a toothpick which is safe to use;

b. to provide a toothpick which does not create discomfort when used;

c. to provide a toothpick which is easy to use, even without a mirror; and d. to provide a toothpick which is effective in cleaning the back of the front teeth.

Still further objects and advantages will become apparent from the ensuing description and drawings.

DETAILED DESCRIPTION

Figure 1:
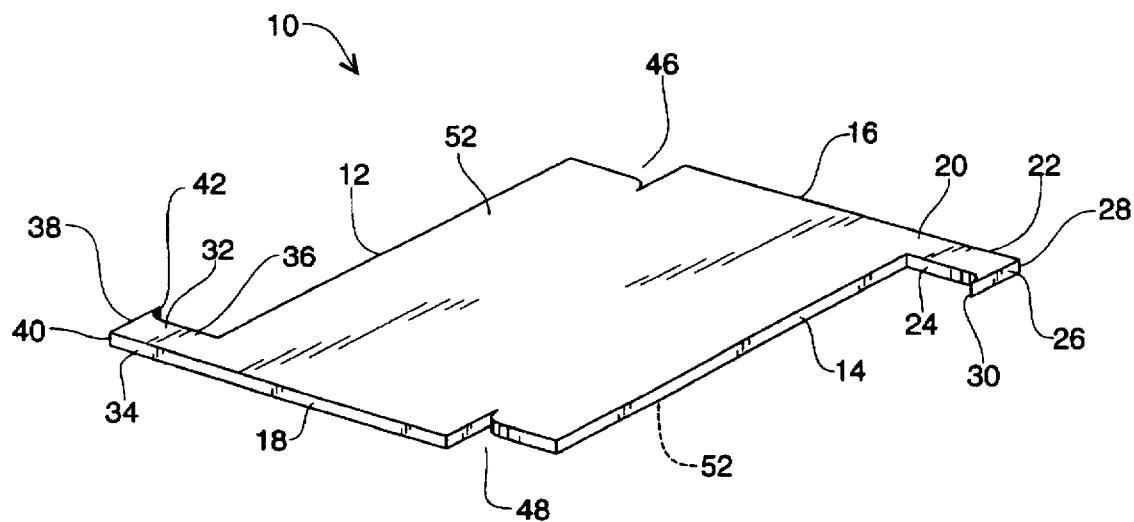
FIG. 1 is a perspective view of the toothpick.
Figure 2:
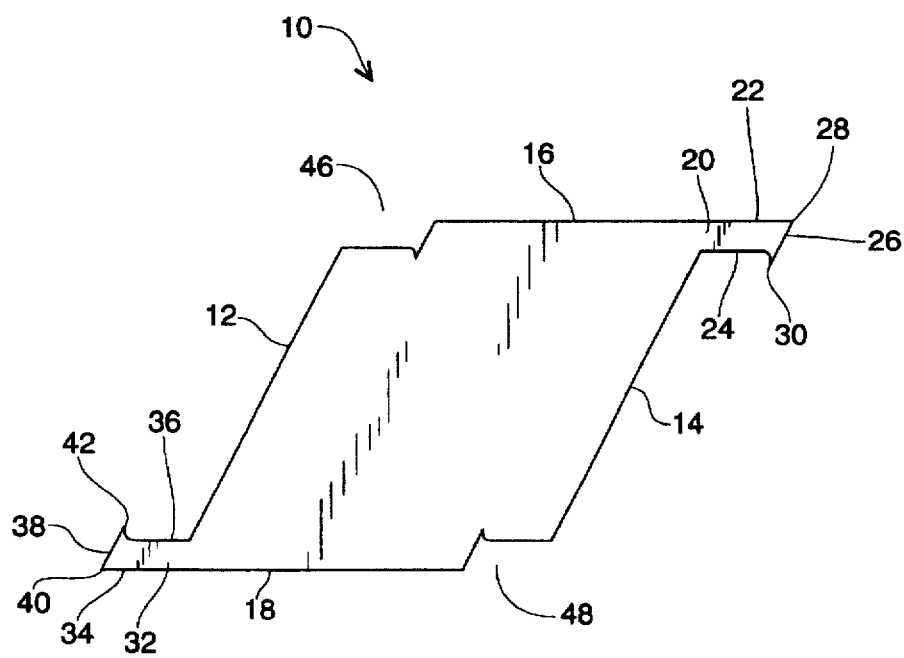
FIG. 2 is an elevational view of the toothpick.

FIG. 1 is a perspective view of a toothpick 10, and FIG. 2 is an elevational view thereof. Referring to FIGS. 1 and 2, the toothpick 10 is substantially planar, and includes a straight first edge 12 which is opposite and parallel to a straight second edge 14. The toothpick further includes a straight third edge 16 positioned at an acute angle with relation to the second edge 14 and a straight fourth edge 18 positioned opposite and parallel to the third edge 16.

A first arm 20 extends outward from the second edge 14. A first arm first edge 22 is co-linear with the third edge 16 and is disposed opposite and parallel to a first arm second edge 24. The first arm first edge 22 turns to form a first distal edge 26 which is parallel to the second edge 14. The intersection of the first arm first edge 22 and the first distal edge 26 forms a first point 28. The first arm second edge 24 extends straight outward from the second edge 14, then curves away from the first arm first edge 22 to form a first barb 30 at the intersection of the first arm second edge 24 and the first distal edge 26.

A second arm 32 extends outward from the first edge 12. A second arm first edge 34 is co-linear with the fourth edge 18 and is disposed opposite and parallel to a second arm second edge 36. The second arm first edge 34 turns to form a second distal edge 38 which is parallel to the first edge 12. The intersection of the second arm first edge 34 and the second distal edge 38 forms a second point 40. The second arm second edge 36 extends straight outward from the first edge 12, then curves away from the second arm first edge 34 to form a second barb 42 at the intersection of the second arm second edge 36 and the second distal edge 38.

The toothpick 10 includes structure forming a first notch 46 adjacent the first edge 12 and the third edge 16, and structure forming a second notch 48 adjacent the second edge 14 and the fourth edge 18.

Figure 3:
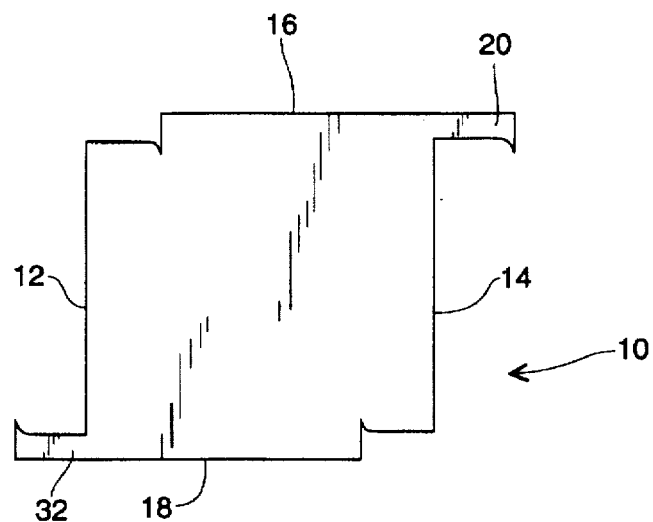
FIG. 3 is an elevational view of an alternative embodiment of the toothpick.

FIG. 3 is an elevational view of an alternative embodiment of the toothpick 10, wherein the first edge 12 and the third edge 16 form a right angle with each other, and the second edge 14 and the fourth edge 18 form a right angle with each other. This embodiment is somewhat more difficult to use than the first embodiment shown in FIGS. 1 and 2, but is within the scope of the present invention.

Figure 4:
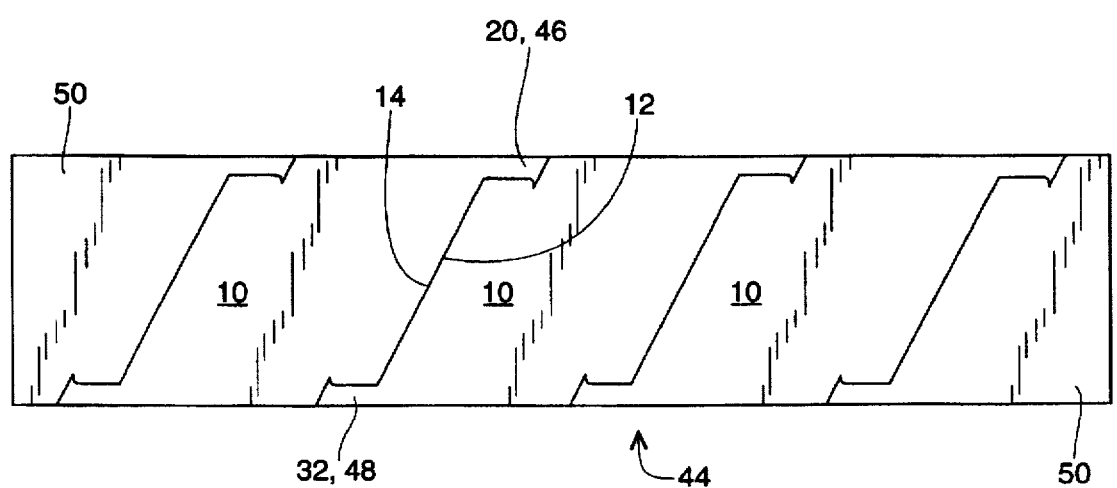
FIG. 4 is an elevational view of a strip of plastic from which multiple toothpicks may be cut as part of the manufacturing process.

FIG. 4 is an elevational view of a strip of plastic 44 from which multiple toothpicks 10 may be cut as part of the manufacturing process. The second edge 14, the first arm 20, and the second notch 48 of the toothpick 10 mate with the first edge 12, the first notch 46 and the second arm 32 respectively of the adjacent toothpick 10. This permits multiple toothpicks 10 to be cut from the strip 44 with a minimum of waste pieces 50. The waste pieces 50 would occur only at the ends of the strip 44; thus, if a large quantity of toothpicks 10 are cut from a single strip 44, the percentage of waste would be quite small.

Figure 5:
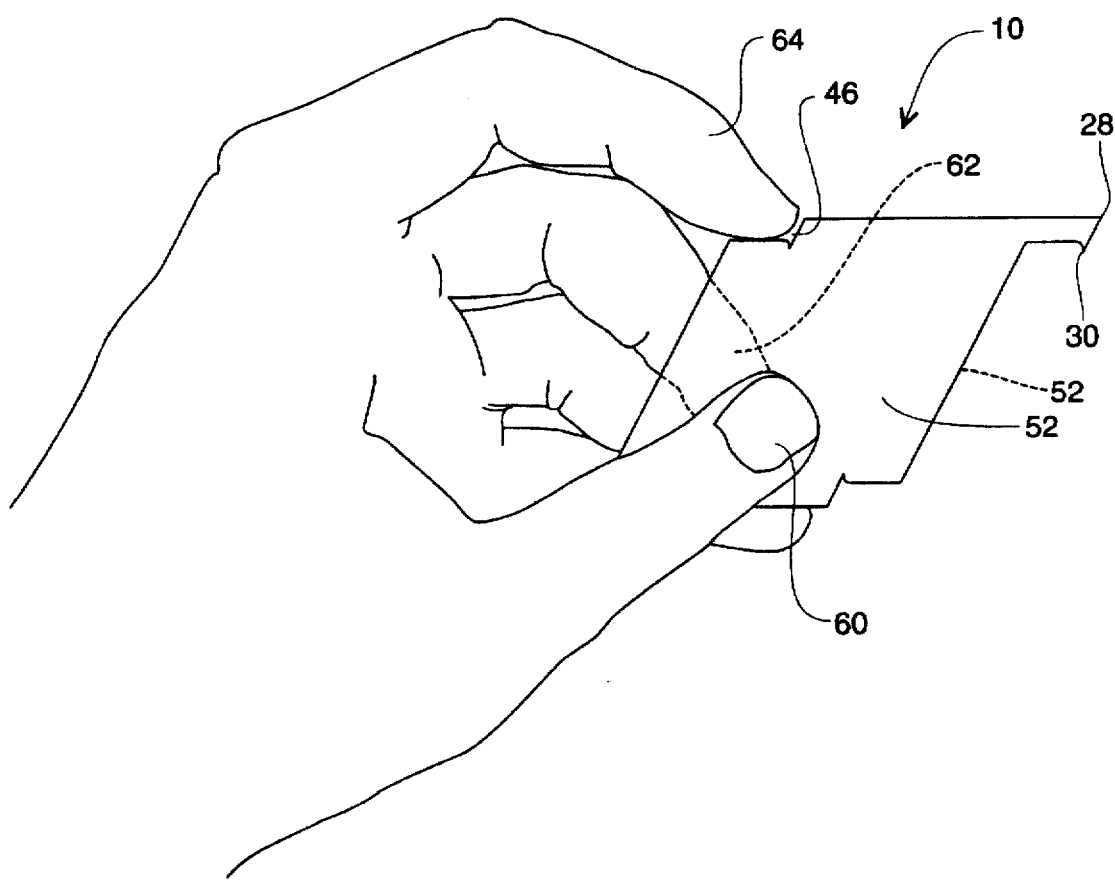
FIG. 5 shows one method of holding the toothpick for use.

FIG. 5 shows one method of holding the toothpick 10 for use. Referring to FIG. 1 and FIG. 5, the toothpick 10 includes two broad opposing surfaces 52. A user places a thumb 60 and a middle finger 62 of a hand on the two broad opposing surfaces 52, thus firmly grasping the toothpick 10 between the thumb 60 and the middle finger 62. The user further places an index finger 64 within the first notch 46. In this position, it is easy to manipulate the toothpick 10 to clean all of the teeth from the front, using the first point 28, and to clean all of the bottom teeth from the rear, using the first barb 30. From this holding position, the user may extend his index finger 64 up to the first arm 20 to manipulate the first arm 20 to assist in the cleaning of the teeth. In the preferred embodiment, the toothpick 10 is made from thin, flexible plastic. This flexibility makes it easy to manipulate the first arm 20 as described. Of course, if rigid plastic or another material is used in the manufacture of the present invention, it would still be within the scope and spirit of the present invention.

Figure 6:
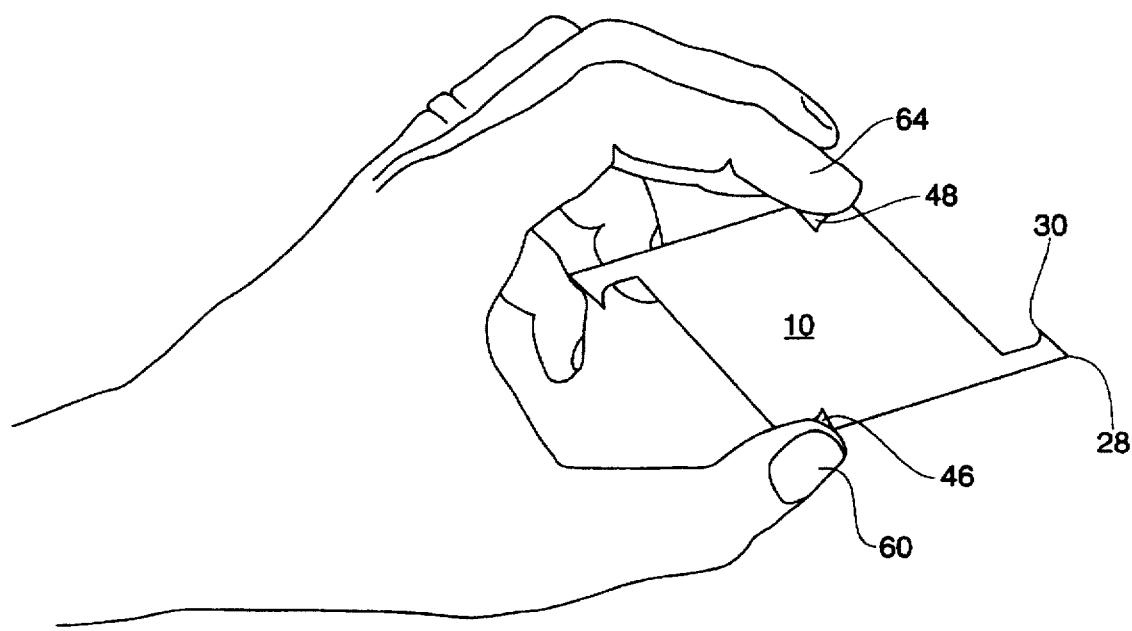
FIG. 6 shows another method of holding the toothpick for use.

FIG. 6 shows another method of holding the toothpick 10 for use. The user places the index finger 64 in the second notch 48 and the thumb 60 in the first notch 46, thus grasping the toothpick 10. In this position, it is easy to manipulate the toothpick 10 to clean all of the teeth from the front, using the first point 28, and to clean all of the top teeth from the rear, using the first barb 30.

Of course, various other methods of holding and manipulating the toothpick 10 are possible.

The second point 40 and the second barb 42 may be used to clean the teeth in the same manner as described for the first point 28 and the first barb 30, by holding the toothpick 10 in the appropriate position therefor.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. The scope of the invention is to be limited only by the following claims and their legal equivalents.

The invention claimed is:

1. A substantially planar toothpick comprising:
   a. a straight first edge which is opposite and parallel to a straight second edge;
   b. a straight third edge which is opposite and parallel to a straight fourth edge;
   c. a first arm extending outwardly from the second edge and having a first arm first edge which is collinear with the third edge and is disposed opposite and parallel to a first arm second edge;
   d. the first arm further including a first distal edge which is parallel to the second edge, the intersection of the first arm first edge and the first distal edge forming a first point; and
   e. the first arm second edge extending straight outward from the second edge, then extending away from the first arm first edge to form a first barb at the intersection of the first arm second edge and the first distal edge.

2. The toothpick of claim 1, further comprising:
   a. a second arm extending outwardly from the first edge and having a second arm first edge which is collinear with the fourth edge and is disposed opposite and parallel to a second arm second edge;
   b. the second arm further including a second distal edge which is parallel to the first edge, the intersection of the second arm first edge and the second distal edge forming a second point; and
   c. the second arm second edge extending straight outward from the first edge, then extending away from the second arm first edge to form a second barb at the intersection of the second arm second edge and the second distal edge.

3. The toothpick of claim 2, further including structure forming a first notch adjacent the first edge and the third edge, and structure forming a second notch adjacent the second edge and the fourth edge.

4. The toothpick of claim 3, wherein the second edge, the first arm, and the second notch mate with the first edge, the first notch and the second arm respectively of an adjacent toothpick, whereby a plurality of the toothpicks may be cut from a single strip of material with a minimum of waste.

5. A substantially planar toothpick comprising:
   a. a first edge which is opposite and substantially parallel to a second edge;
   b. a third edge which is opposite and substantially parallel to a fourth edge;
   c. a first arm extending outwardly from the second edge and having a first arm first edge which is substantially collinear with the third edge and is disposed opposite and substantially parallel to a first arm second edge;
   d. the first arm further including a first distal edge, the intersection of the first arm first edge and the first distal edge forming a first point; and
   e. the first arm second edge extending outward from the second edge, then extending away from the first arm first edge to form a first barb at the intersection of the first arm second edge and the first distal edge.

6. The toothpick of claim 5, further comprising:
   a. a second arm extending outwardly from the first edge and having a second arm first edge which is substantially collinear with the fourth edge and is disposed opposite and substantially parallel to a second arm second edge;
   b. the second arm further including a second distal edge which is substantially parallel to the first edge, the intersection of the second arm first edge and the second distal edge forming a second point; and
   c. the second arm second edge extending outward from the first edge, then extending away front the second arm first edge to form a second barb at the intersection of the second arm second edge and the second distal edge.

7. The toothpick of claim 6, further including structure forming a first notch adjacent the first edge and the third edge, and structure forming a second notch adjacent the second edge and the fourth edge.

8. The toothpick of claim 7, wherein the second edge, the first arm, and the second notch mate with the first edge, the first notch and the second arm respectively of an adjacent toothpick, whereby a plurality of the toothpicks may be cut from a single strip of material with a minimum of waste.

* * * * *